US012551899B2

(12) United States Patent
Park et al.

(10) Patent No.: US 12,551,899 B2
(45) Date of Patent: Feb. 17, 2026

(54) PORTABLE DEVICE FOR LAMP PCR

(71) Applicant: Bioacts Corporation, Incheon (KR)

(72) Inventors: Jin Woo Park, Incheon (KR); Bong Kyun Kim, Incheon (KR); So Young Kim, Incheon (KR)

( * ) Notice: Subject to any disclaimer, the term of this patent is extended or adjusted under 35 U.S.C. 154(b) by 796 days.

(21) Appl. No.: 17/892,055

(22) Filed: Aug. 20, 2022

(65) Prior Publication Data

US 2024/0058820 A1 Feb. 22, 2024

(51) Int. Cl.
*B01L 7/00* (2006.01)
*C12Q 1/689* (2018.01)

(52) U.S. Cl.
CPC ................ *B01L 7/52* (2013.01); *C12Q 1/689* (2013.01); *B01L 2200/147* (2013.01); *B01L 2300/042* (2013.01); *B01L 2300/1805* (2013.01); *B01L 2300/1883* (2013.01)

(58) Field of Classification Search
CPC ................ B01L 7/52; B01L 2200/147; B01L 2300/042; B01L 2300/1805; B01L 2300/1883; B01L 2300/043; B01L 2300/0609; B01L 2300/0809; B01L 9/06; C12Q 1/689
See application file for complete search history.

(56) References Cited

FOREIGN PATENT DOCUMENTS

KR 20210147545 A * 12/2021 ................ B01L 7/52

OTHER PUBLICATIONS

Misawa et al, Application of loop-mediated isothermal amplification technique to rapid and direct detection of methicillin resistant *Staphylococcus aureus* (MRSA) (Year: 2007).*

* cited by examiner

*Primary Examiner* — Narayan K Bhat

(57) ABSTRACT

Provided is a portable isothermal amplification device for amplifying a nucleic acid using an isothermal amplification method, the device comprising: a tube insertion part into which a PCR tube is to be inserted, which is provided in an upper portion of the portable isothermal amplification device; a cover for covering the tube insertion part; a storage space for accommodating a heating device and a storage space cover for blocking the storage space from an outside, which is provided in a lower portion of the portable isothermal amplification device; and a heat insulator for blocking heat from the outside and a heat-sensing sticker capable of measuring a temperature of heat generated by the heating device, which is provided inside the storage space.

7 Claims, 2 Drawing Sheets

PORTABLE DEVICE FOR LAMP PCR

BACKGROUND

Field

The present disclosure relates to a portable isothermal nucleic acid amplifier, and more specifically, a portable nucleic acid isothermal amplifier that anyone can quickly detect in the field in diagnosing the presence or absence of disease or viral infections by detecting biological materials or microorganisms.

Discussion of the Related Art

In general, in order to diagnose the presence of a disease or infection such as a virus by detecting a biological material or microorganism, after collecting a sample, the genetic information of nucleic acids such as trace amount of DNA and RNA contained in the sample is analyzed as much as necessary for the analysis. Therefore, it needs to be amplified in large quantities.

To this end, various methods are applied to amplify the nucleic acid contained in the sample.

As a method of amplification of nucleic acids, the methods of isothermal amplification such as LCR (Ligase Chain Reaction), SDA (Strand Displacement Amplification), NASBA (Nucleic Acid Sequence-Based Amplification), and LAMP (Loop-mediated isothermal amplification) method, and a non-isothermal amplification method such as polymerase chain reaction (PCR) are mainly used.

The polymerase chain reaction, which is a representative example of the non-isothermal amplification method, proceeds in a series of temperature enzymatic reaction steps such as denaturation, annealing, and extension.

For obtaining high yield of high-quality nucleic acids, each of these reaction steps must be carried out in a certain temperature range.

In both the isothermal amplification method and the non-isothermal amplification method, maintaining the reaction temperature constantly is an important factor for obtaining desirable results.

In order to maintain a constant reaction temperature as described above, in the case of a conventional portable nucleic acid amplifier, the power is supplied by a capacitor or the like in the portable amplifier, and an optical element that generates heat by the power is provided to maintain the temperature of the portable amplifier, which is the way in conventional method.

Compared to the conventional methods, the object of the present disclosure is to provide a portable isothermal amplifier capable of maintaining a reaction temperature without using an optical element that generates heat by the power source as described above.

SUMMARY

The present disclosure provides a portable isothermal amplification nucleic acid amplifier for quickly and accurately determining disease diagnosis and virus infection in the field by detecting a biological material or microorganism.

For the objectives, a power supply which is capable of maintaining a constant reaction temperature of the amplifier without using an optical element is applied. In other words, the objectives of the present disclosure include providing a portable nucleic acid isothermal amplifier capable of operating the amplifier using a portable heating device without using an optical element or the like.

In order to solve the above problems, the present disclosure proposes a tube holder and a lid for fixing a plurality of PCR tubes from which samples are collected on the upper part of the amplifier provided in the present disclosure, and heating device such as a hand warmer is provided on the lower part of the amplifier.

The present disclosure also proposes a storage space into which the heating device can be inserted.

The portable nucleic acid isothermal amplifier provided by the present disclosure is a device that can rapidly amplify target nucleic acids contained in a sample collected in the field and anyone can use it conveniently.

In addition, in order to maintain the reaction temperature in the present disclosure, it is easy to use it because it is possible to maintain the reaction temperature by using a simple heating device such as a hand heater that is easily accessible without using a complex heating device by supplying power and optical elements that have been conventionally applied.

BRIEF DESCRIPTION OF DRAWINGS

The above and other aspects, features and other advantages of the present aspects will be more clearly understood from the following detailed description taken in conjunction with the accompanying drawings, in which.

BRIEF DESCRIPTION OF EMBODIMENTS

Figure 1:
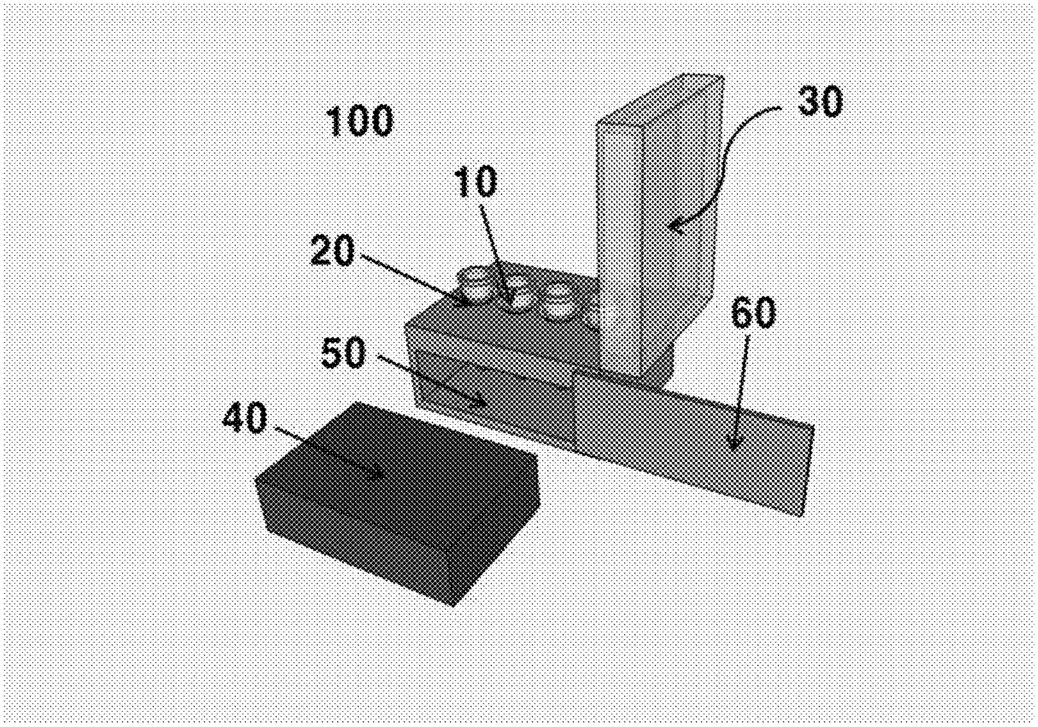
FIG. 1 shows a portable isothermal amplifier provided in exemplary embodiments of the present invention.

Hereinafter, preferred embodiments of the present invention will be described in detail with reference to the accompanying drawings.

In addition, the terms or words used in the present specification and claims are not to be construed as being limited to their ordinary or dictionary meanings and the inventor may properly define the concept of the terms or words in order to best describe his invention. Based on the principle, the terms and words should be interpreted as meanings and concept consistent with the technical idea of the present invention.

Therefore, since the configurations shown in the embodiments and drawings described in this specification are only the most preferred embodiment of the present invention and do not represent all of the technical spirit of the present invention, it should be understood that various equivalents and modifications may be substituted for them at the time of filing the present application.

In order to diagnose infection of microorganisms or viruses in the field, such as hospitals or clinics, after obtaining a sample from the field using a tube and we should transfer it to a laboratory that detects the microorganism or virus. And after amplifying the nucleic acid contained in the tube using an isothermal PCR amplifier provided in the laboratory, we can diagnose it through a detection method such as fluorescence diagnosis.

Therefore, there is a possibility that the sample collected at the site may be contaminated or transformed during the above process. For this reason, in order to solve this problem, it is important to quickly detect the microorganism or virus at the site.

In order to solve the above problems, the portable isothermal amplification device (100) provided in exemplary embodiments of the present invention may use a PCR tube capable of amplifying a target nucleic acid contained in the sample obtained in the field.

In accordance with exemplary embodiments of the present invention, a heating device capable of maintaining a constant reaction temperature may be provided inside the portable isothermal amplifier so that the nucleic acid is efficiently amplified during the amplification process.

The portable isothermal amplification device (100) provided by exemplary embodiments of the present invention relates to a portable isothermal amplifying device capable of rapidly detecting microorganisms and viruses in a field such as a hospital or public health center.

The portable isothermal amplification device (100) in accordance with exemplary embodiments of the present invention is characterized by applying a ring-mediated isothermal amplification method (LAMP) when amplifying a nucleic acid to be detected using a PCR method.

The portable isothermal amplification device (100) in accordance with exemplary embodiments of the present invention may have a PCR tube insertion unit (20) at the top which is capable of fixing the PCR tube (10) containing the sample.

In addition, the portable isothermal amplification device (100) in accordance with exemplary embodiments of the present invention may also have a tube cover (30) for fixing the PCR tube (10) after inserting the PCR tube (10) at the top.

Additionally, in the lower part of the portable isothermal amplification device (100) provided in exemplary embodiments of the present invention, there is formed a storage space (50) for accommodating the heating device (40) such as a hand warmer for maintaining a constant reaction temperature, which is the most important condition for amplifying the nucleic acid contained in the PCR tube (10) by the LAMP method.

A storage space cover (60), which can block the storage space (50) from the outside, may be provided so that the heat generated by the heat-generating device (40) is maintained only inside the portable isothermal amplifier (100) in accordance with exemplary embodiments of the present invention.

The PCR tube (10) in the inside of the portable isothermal amplification device (100) provided in exemplary embodiments of the present invention may contain a PCR amplification reagent for amplifying a target nucleic acid such as DNA or RNA contained in the sample and a probe for detecting the target nucleic acid and diagnostic reagents composed of fluorescent substances.

Therefore, after taking a sample from the field, the sample is put into the PCR tube (10), and the tube (10) is inserted into the portable isothermal amplification device (100) provided in exemplary embodiments of the present invention. For the fluorescent solutions in the PCR tube (10), after a certain time has elapsed, there is a color change of the reagent in the tube (10) because the nucleic acid contained in the PCR tube (10) is amplified isothermally in the amplifying device (100) which amplifies the nucleic acid contained in the PCR tube (10) isothermally and reacts with the probe in the tube (10).

By using such a color change, the presence of a specific microorganism or virus contaminated in the sample can be rapidly confirmed at the field, and whether the field is infected by the microorganism or virus can be rapidly identified.

The reagent that is put into the inside of the PCR tube (10) mounted inside the portable isothermal amplification device (100) provided in exemplary embodiments of the present invention includes a PCR amplification reagent capable of amplifying any type of target nucleic acid and diagnostic reagents capable of detecting the target nucleic acid.

Therefore, the portable isothermal amplifier (100) provided in exemplary embodiments of the present invention can be applied to any kinds of microorganism or virus suspected of being infected in the field depending on the reagents injected into the PCR tube (10).

In the portable isothermal amplification device (100) provided in exemplary embodiments of the present invention, the heating device (40) for providing heat for PCR amplification of the nucleic acid of the sample contained into the PCR tube (10) may be a hand warmer, a heating pack, a heating pad, etc.

The heating device can be directly inserted into the storage space (50) provided in the portable isothermal amplification device (100) in accordance with exemplary embodiments of the present invention.

In addition, as the heating device (40), any heating composition capable of using heat-generator through oxidation of iron can be directly put into the storage space (50) and the heating composition can be a solid composition comprising iron powder, salt, activated carbon, sawdust, vermiculite, diatomaceous earth and water and the like.

The exothermic heating composition uses heat generated in the oxidation process of iron when iron powder meets oxygen and water.

In addition, as the heating composition, a liquid heating composition may be used, and the liquid composition includes sodium thiosulfate or sodium acetate and a metal piezoelectric body.

The heat generating device used in exemplary embodiments of the present invention can be any suitable heat generating device as long as it can be accommodated in the storage space (50).

Figure 2:
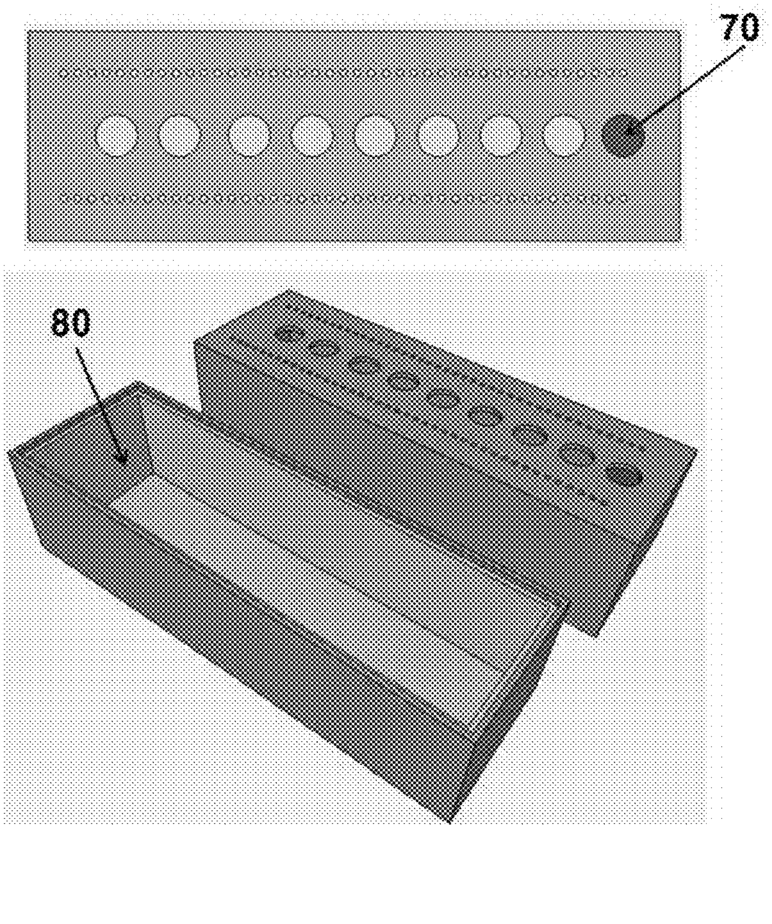
FIG. 2 illustrates a storage space of the portable isothermal amplification device provided in exemplary embodiments of the present invention.

FIG. 2 shows the storage space (50) of the portable isothermal amplifier (100) provided in exemplary embodiments of the present invention.

The upper drawing of FIG. 2 shows a plan view of the storage space (50), and inside of the storage space (50), there is a heat-sensing sticker (70) capable of measuring the temperature of the heating device (40) provided inside the storage space (50).

The heat-sensing sticker (70) is installed in contact with the heat-generating device (40) at the upper portion of the storage space (50), and the temperature of the heat generated from the heat-generating device (40) can be measured by the heat-sensing sticker 70.

The heat-sensing sticker (70) changes the color smoothly during the heating process. However, when the temperature exceeds a certain temperature (e.g., about 60° C.), the heat-sensing sticker (70) completely changes into another color, which can prove the isothermal amplification of the hexanes in the sample.

Such a change in temperature can be observed with naked eyes by the heat-sensing sticker (70). For example, when the heat-sensing sticker (70) which was white shows red color due to the heat generated by the heating device (40), it verifies that the isothermal amplification of the nucleic acid is actively occurring.

The lower view of FIG. 2 is a separate view of the storage space (50). An insulating material (80) is provided at the lower portion of the interior of the storage space (50), so that heat generated from the heating device is prevented from escaping to the outside. As the result, it makes sure that efficient isothermal amplification of nucleic acids is performed in the PCR tube (10).

Examples

Next, an embodiment in which methicillin-resistant *Staphylococcus aureus* (MRSA) is detected using the portable isothermal amplification device (100) in accordance with exemplary embodiments of the present invention will be described.

In order to detect MRSA using the portable isothermal amplification device provided in exemplary embodiments of the present invention, 25 μl of a reagent in which the concentration of MRSA was changed was injected into the PCR tube (10) and as the exothermic heating device, a solid heat generating means made of iron powder, activated carbon, sodium chloride, vermiculite and a highly hygroscopic polymer was put into the storage space (50).

While the reaction proceeded, the change in the color of the reagent injected into the PCR tube (10) was observed at intervals of 5 minutes after the reaction was 25 minutes.

Figure 3A:
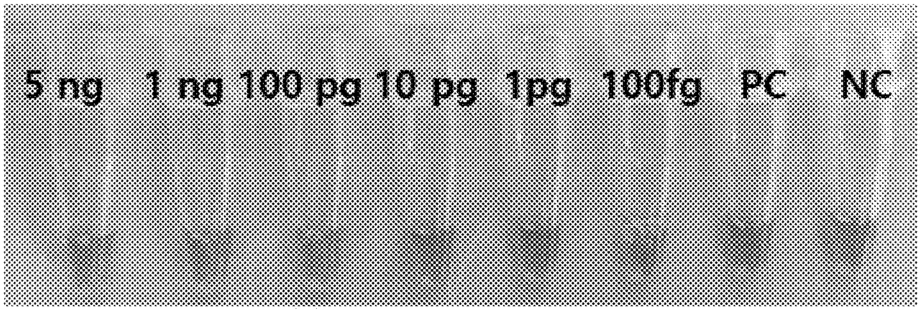
FIGS. 3*a* and 3*b* show the results of experiments for detecting MRSA using the portable isothermal amplifier provided in exemplary embodiments of the present invention.
Figure 3B:
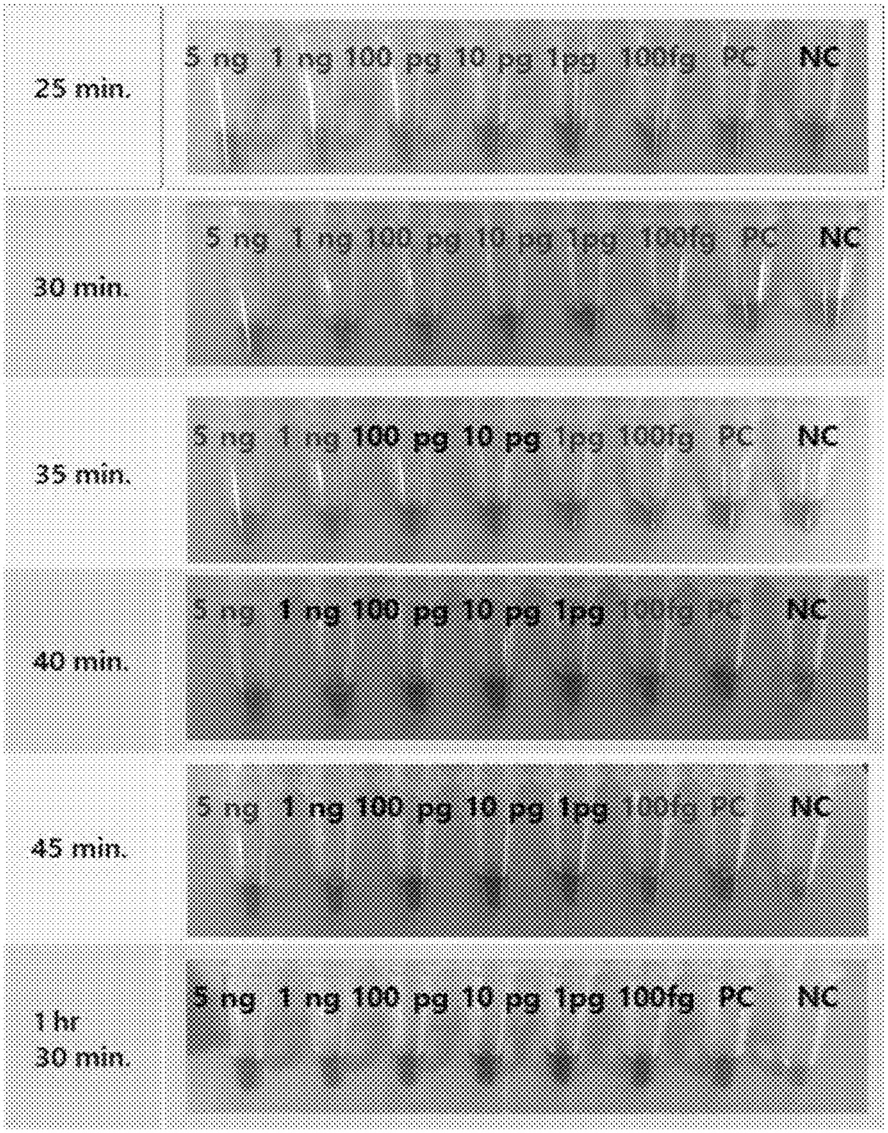

As shown in FIGS. 3*a* and 3*b*, when MRSA could be easily and quickly detected using the portable isothermal amplification device provided in exemplary embodiments of the present invention, although the concentration of MRSA was extremely small.

In FIGS. 3*a* and 3*b*, each number represents the concentration of MRSA contained in the PCR tube (10), while PC represents a positive control, NC represents a negative control.

FIG. 3*a* shows the state before inserting the PCR tube (10) into the portable isothermal amplifier (100), and FIG. 3*b* shows the time after inserting the PCR tube (10) into the portable isothermal amplifier (100) and the color change of the reagent according to the concentration of MRSA.

Although the present invention has been described with reference to the above embodiments and drawings, it is known to those skilled in the art that the technical spirit of the present invention is not limited by the above embodiments and can be extended to all configurations including the technical features of the present invention.

The invention claimed is:

1. A portable isothermal amplification device for amplifying a nucleic acid using a ring-mediated isothermal amplification method, the device comprising:

- a tube insertion part into which a PCR tube is to be inserted, which is provided in an upper portion of the portable isothermal amplification device;
- a cover for covering the tube insertion part;
- a storage space for accommodating a heating device and a storage space cover for blocking the storage space from an outside, which is provided in a lower portion of the portable isothermal amplification device;
- a heat insulator for blocking heat from the outside; and
- a heat-sensing sticker capable of measuring a temperature of heat generated by the heating device, which is provided inside the storage space.

2. The portable isothermal amplification device of claim 1, wherein the heating device comprises a hand warmer comprising iron powder, salt, activated carbon, sawdust, vermiculite, water, or a combination thereof.

3. The portable isothermal amplification device of claim 1, wherein the heating device comprises a liquid heating comprises comprising sodium thiosulfate, sodium acetate, or a combination thereof.

4. The portable isothermal amplification device of claim 1, wherein the nucleic acid is a nucleic acid extracted from methicillin-resistant *Staphylococcus aureus*.

5. The portable isothermal amplification device of claim 1, wherein the portable isothermal amplification device does not comprise a power source connected to the heating device.

6. The portable isothermal amplification device of claim 1, wherein the heating device does not comprise a heater operable by supplied power.

7. The portable isothermal amplification device of claim 1, wherein the heat-sensing sticker is provided in contact with the heating device at an upper portion of the storage space to measure heat generated by the heating device.

* * * * *